United States Patent [19]
Kwong et al.

[11] Patent Number: 5,381,351
[45] Date of Patent: Jan. 10, 1995

[54] AMBULATORY MONITOR ECG PULSE CALIBRATION METHOD

[75] Inventors: Manlik Kwong, Beaverton; Edward L. Feldhousen, Tualatin; Dennis E. Ochs, McMinnville, all of Oreg.

[73] Assignee: Hewlett-Packard Corporation, Palo Alto, Calif.

[21] Appl. No.: 137,441

[22] Filed: Oct. 15, 1993

[51] Int. Cl.⁶ .................................................. G01C 25/00
[52] U.S. Cl. .............................. 364/571.04; 128/697; 364/413.06; 364/737; 364/224.6; 364/922.3; 360/25; 360/31
[58] Field of Search ............ 128/711, 696, 695, 697; 346/25, 33 R; 371/1, 68.1, 68.2, 68.3; 360/25, 26, 31; 364/224.6, 554, 571.04, 413.06, 487, 737, 922.3

[56] References Cited

U.S. PATENT DOCUMENTS

| | | | |
|---|---|---|---|
| 4,031,367 | 6/1977 | Murphy | 235/151.3 |
| 4,506,309 | 3/1985 | Joannou et al. | 360/26 |
| 4,883,065 | 11/1989 | Kelen | 128/711 |
| 4,999,772 | 3/1991 | Bowman et al. | 364/413.05 |
| 5,121,260 | 6/1992 | Asakawa et al. | 360/25 |
| 5,205,295 | 4/1993 | Del Mar et al. | 128/711 |
| 5,305,202 | 4/1994 | Gallant et al. | 364/413.06 |

*Primary Examiner*—Emanuel T. Voeltz
*Assistant Examiner*—Craig Steven Miller

[57] ABSTRACT

An ECG waveform calibration method combines ECG channel calibration pulses to form combined calibration pulses. The combined channel pulses are filtered to select valid combined pulses. The selected combined pulses are correlated to the corresponding channel calibration pulses to determine valid channel calibration pulses from which a correction scale factor is derived. A valid calibration pulse is determined where a correlation between a combined calibration pulse and a corresponding channel calibration pulse is greater than a predetermined correlation value. The valid channel calibration pulses are then characterized. A set of valid channel calibration pulses is selected for each channel based on the characterization to form an average calibration pulse. The average calibration pulse is used to determine a correction scale factor for each channel which is used to scale the actual channel ECG waveform data. The method also includes a step for adjusting the intra-channel skew.

16 Claims, 7 Drawing Sheets

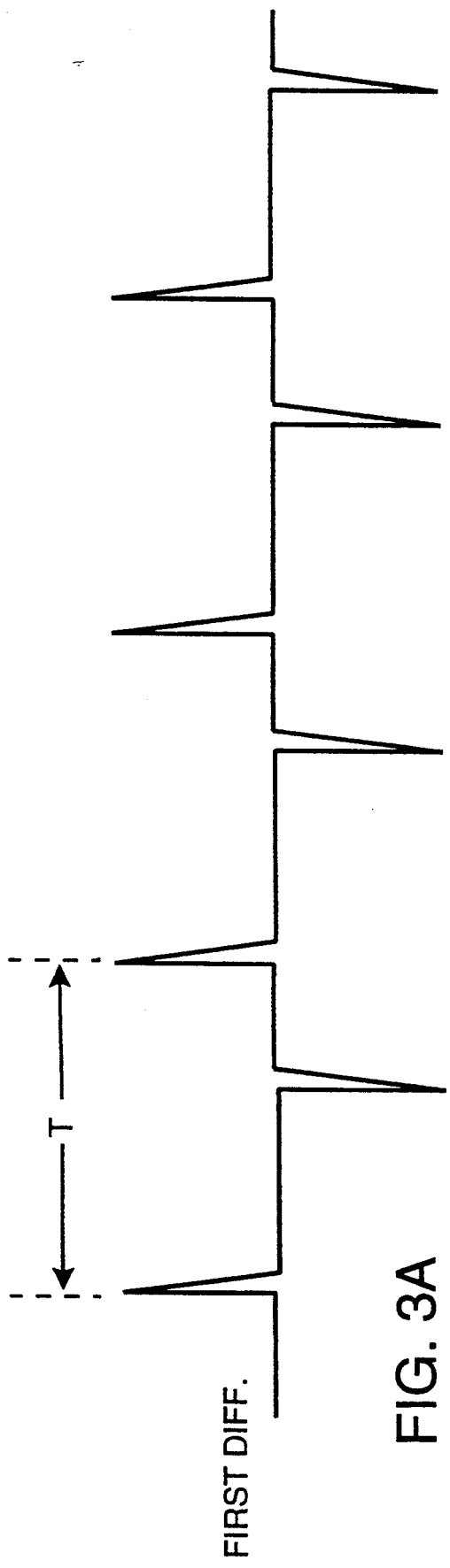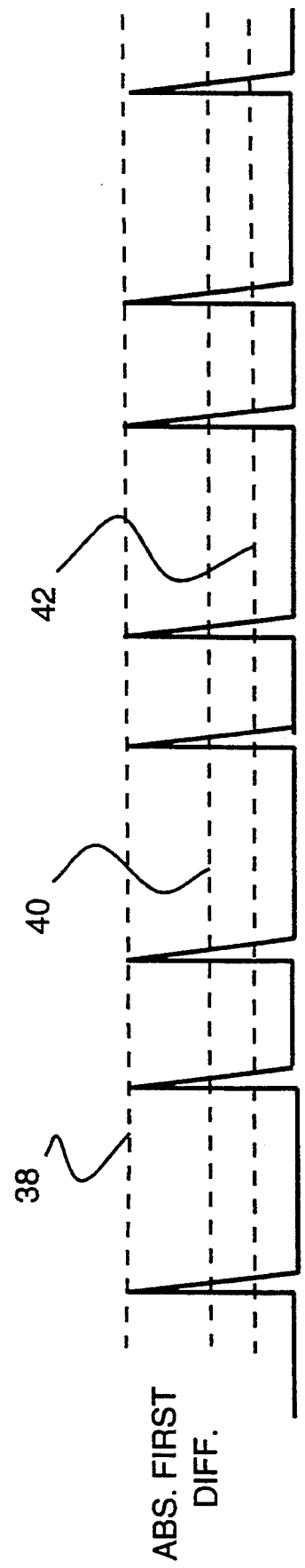
FIG. 3A
FIG. 3B

AMBULATORY MONITOR ECG PULSE CALIBRATION METHOD

BACKGROUND OF THE INVENTION

The present invention relates to methods and apparatus for recording and playing back EGG signals and more particularly to such methods and apparatus in which the EGG signals are processed to compensate for variations in amplitude and phase of the EGG signals due to the recording process.

Prior art systems, known as Holter recorders and playback systems, record EGG signals which are provided from a patient via electrodes to a small recorder carried by the patient. The EGG signals are continuously recorded on an analog tape typically over a 24 hour period. Several prior art systems use a conventional C60 analog cassette tape of the type typically used to record audio information. In order to do so, the tape must be slowed down approximately 1/50th of normal audio speed. Usually three channels of EGG data are recorded plus a fourth channel which includes a timing signal that is generated by the recorder.

After recording, the tape is played back on a device which runs the tape at high speed and processes the analog signals derived from the tape. Such processing typically includes filters which are intended to compensate for dropoff at both the low and high frequencies and for phase distortion which results from the magnetic recording and playback process. The filtered signals are digitized and further processed into a report for analysis by a physician. Typically, the digitized data is transmitted to a personal computer connected to the playback system for further analysis.

The data transmitted to the personal computer, however, can exhibit phase and magnitude distortion due to non-linearities in the recording and playback systems. Moreover, the phase and magnitude distortion produced by a system for recording and playing back ECG signals can vary over time. It can vary as a result of wear on the heads for recording and playing back the signal. It can also vary in response to misalignment of the mechanical components which affect the record and playback head compliance with the tape. Independently of time, distortion can vary as a result, e.g., of using an analog tape having a different thickness or type of tape coating thereon.

Prior art techniques for calibrating the ECG recorder include recording a series of rectangular calibration pulses of known amplitude on each of three channels used the recording ECG signals. Pulses are played back through a playback deck and passed through analog compensation filters to restore the pulse's original phase and frequency content. The playback unit is calibrated by measuring the amplitude of the calibration pulses and thereafter generating a data scaler which is applied to the ECG data.

There are several problems with this approach. One is that phase and magnitude distortion can vary from channel to channel. Another problem results from a phenomenon called tape dropout. Tape dropout is an apparent reduced recording level on a tape caused by variations in the recording medium. When such areas are encountered during the calibration process, accuracy of calibration is adversely affected.

Accordingly, a need remains for a more accurate method of calibrating each ECG channel.

SUMMARY OF THE INVENTION

It is, therefore, an object of the invention to accurately calibrate ECG channels.

Another object of the invention is to correct inter-channel skew of the ECG waveform data.

An ECG waveform calibration method according to the invention forms a combined channel of calibration data from the ECG channel data from which valid channel calibration pulses are detected. The transitions of the combined channel pulses are detected and filtered to determine valid combined channel pulse transitions. The valid combined channel pulse transitions are used to detect valid combined channel calibration pulses where the transitions exhibit a predetermined relationship. The valid combined channel calibration pulses are correlated to the channel calibration pulses to determine valid channel calibration pulses. The valid channel calibration pulses are then characterized as either normal, semi-normal or double-exponential. Depending on the characterization, a set of valid channel calibration pulses is selected for each channel to form an average calibration pulse. The average calibration pulse is used to determine a correction scale factor for each channel which is used to scale the actual channel ECG waveform data.

In another aspect of the invention, the valid channel calibration pulses are used to determine the inter-channel skew of the ECG waveform data. The skew is thereafter corrected by phase shifting the actual ECG waveform data by the skew amount.

In a further aspect of the invention, the onset and the offset of the calibration pulses is determined where there are a predetermined number of consecutive valid combined calibration pulses relative to the beginning and end of the combined calibration pulses, respectively.

An advantage of the present invention is the calibration method compensates for differences in recording conditions.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 3A is a graphical representation of a first difference signal generated from the combined channel pulses of FIG. 2.

FIG. 3B is a graphical representation of an absolute first difference signal generated from the combined channel pulses of FIG. 2.

DETAILED DESCRIPTION

Figure 1:
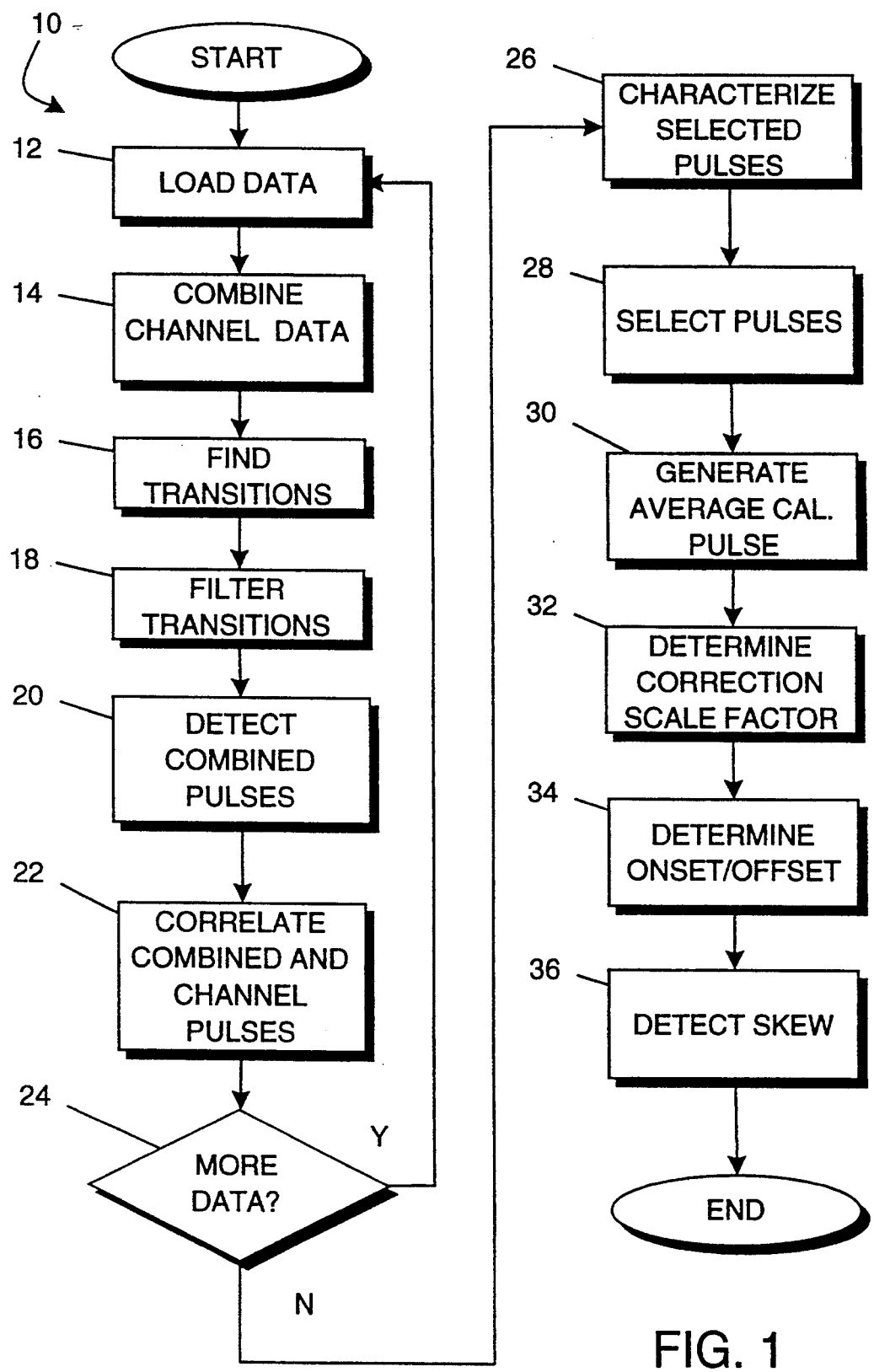
FIG. 1 is a top level flow chart of the calibration method according to the invention.

Referring to FIG. 1, a top level flow chart 10 of a method of calibrating an ECG ambulatory monitor is shown. In the preferred embodiment the method is executed on a microprocessor in a personal computer. The personal computer is connected to a playback recorder and receives digitized EGG waveform data therefrom. Alternatively, the calibration method can be executed within the playback system itself. In the latter case, the actual ECG waveform data is calibrated before the waveform data is transmitted to the personal computer for analysis.

The method shown in FIG. 1 begins by loading EGG waveform in step 12. The EGG data processed by the method is first in a digital format. Thus, if the ECG data is read off a magnetic tape in an analog format, the analog waveform data must first be converted to a digital format using a digital to analog converter before step 12 can be executed. In the preferred embodiment, the data consists of three channels of non-interleaved ECG waveform data. The data in a particular channel corresponds to data recorded from a corresponding sensor. A beginning portion of the waveform, however, corresponds to the calibration period during which time calibration pulses are recorded.

In the preferred embodiment, the load data step 12 loads a predetermined amount of the ECG data e.g. one second of ECG data. Thus, the calibration method described hereinafter operates on a subset of the ECG data at any one time. After the data subset is processed, a second predetermined amount of the ECG data is loaded and the calibration method is repeated with respect to that subset, as shown in step 24. Loading a subset of the ECG data requires significantly less memory than loading in all of the ECG data at one point. Alternatively, all of the ECG data corresponding to the calibration period can be loaded in step 12 where there are no memory constraints.

Figure 2:
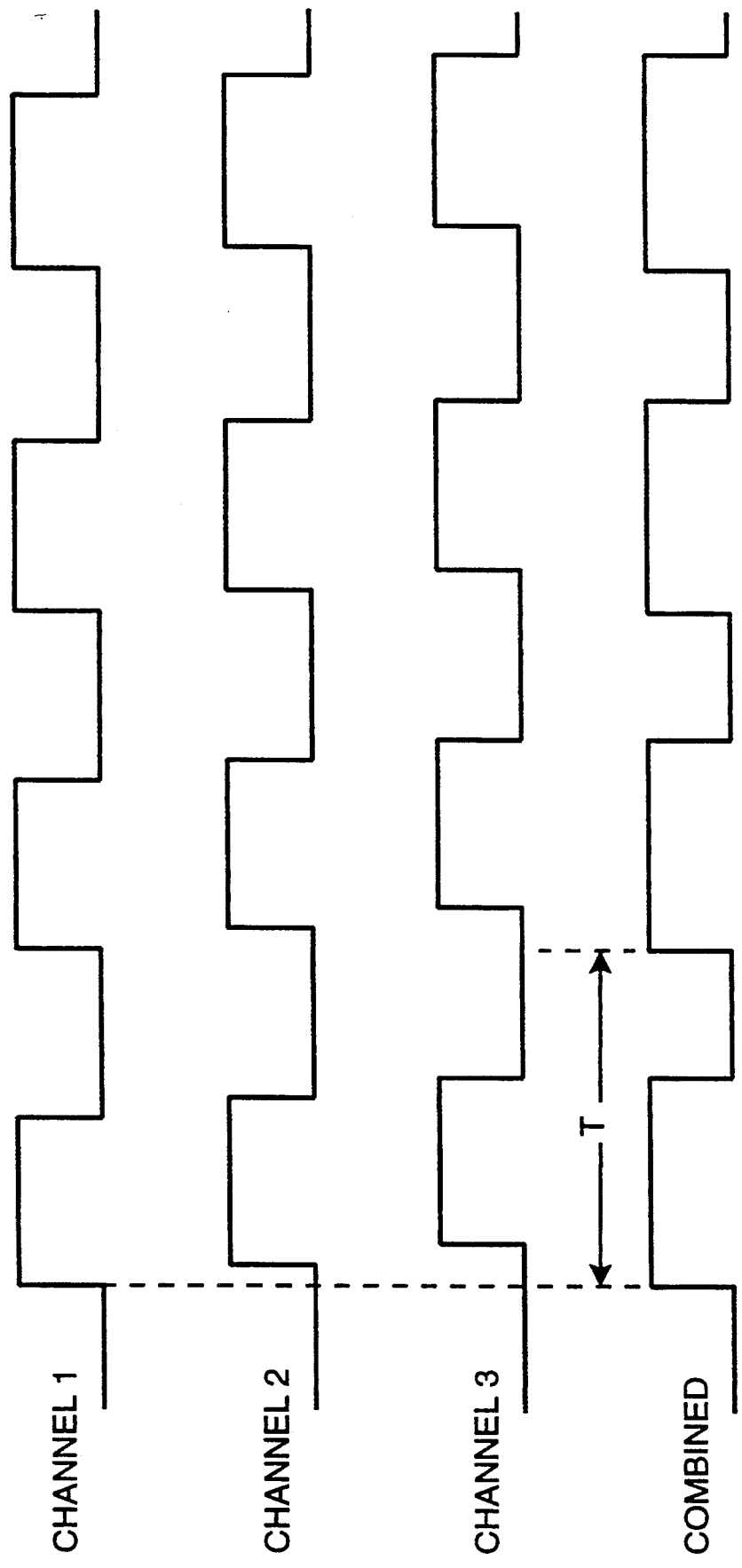
FIG. 2 is a graphical representation of recorded channels of EGG calibration pulses and a combined channel of EGG calibration pulses generated according to the invention.

The EGG data loaded in step 12, therefore, consists of a predetermined amount of calibration data for each of the channels. In step 14, the calibration data from each channel is combined to form a combined calibration channel. Referring now to FIG. 2, three channels of calibration data are shown, i.e., CHANNELS 1-3. The calibration data shown in FIG. 2 corresponds to the predetermined amount of EGG data loaded in step 12. The waveforms are shown as continuous in FIG. 2, however, the waveforms are comprised of a plurality of discrete samples taken at regular intervals. Although the three channels record the same series of calibration pulses, differences in channel length and impedance produces differences in the phase and amplitude of the calibration pulses recorded on each channel. Also shown in FIG. 2 is the corresponding combined channel which is the sum of CHANNELS 1-3. In the preferred embodiment, the calibration method uses a sum of absolute value method across all three channels to form the combined channel. The sum of absolute value approximates an absolute vector magnitude of the calibration pulses. Alternatively, the absolute vector magnitude can be computed, however, the absolute vector magnitude computation is significantly more computationally intensive.

The combined channel data produced in step 14 is use to identify transitions of the calibration pulses in step 16. Before identifying the transitions, however, step 16 first checks for a sufficient level of activity within the predetermined amount of data. The method calculates an absolute mean amplitude for the predetermined period. If the absolute mean amplitude is less than a predetermined minimum, e.g., one millimeter, then no further processing is performed. In that case, load step 12 is repeated (not shown in FIG. 1). If, however, there is a sufficient level of activity, the combined channel is differentiated to identify transitions in the combined channel data. Referring to FIG. 3A, a first difference of the combined channel shown in FIG. 2 is shown. The leading edge of the combined pulses has a positive first difference, and the trailing edge has a negative first difference, as shown in FIG. 3A.

The transitions identified in step 16 are filtered in step 18 to eliminate spurious transitions. The transitions are filtered by first taking the absolute value of the first difference signal. A resulting absolute first difference signal is shown in FIG. 3B. Once the absolute values are determined, a maximum peak transition value 38 is determined from the absolute first difference. The maximum peak transition value equals a maximum transition value of the absolute first difference transitions. From the maximum peak transition value 38, a half-maximum peak transition value 40 and a quarter-maximum peak transition value 42 are determined. Any absolute first difference transition having a peak value less than the quarter-maximum peak transition value 42 is then zeroed from the first difference.

The remaining first difference transitions are further filtered to leave only valid combined pulse transitions. The first difference transitions having peaks greater than one-half maximum peak transition value are marked by an onset time, an offset time, and a polarity. The onset time corresponds to a beginning point of a leading edge of a transition. An offset corresponds to an endpoint of a trailing edge of the transition. The polarity is either positive or negative based on whether the transition is a positive transition or a negative transition. The onset and offset times are then used to further filter the first difference transitions as follows.

The method assumes that valid combined pulse transitions are separated by more than a predetermined amount of time. In the preferred embodiment, a hysteresis of 32 ms is required to separate valid combined pulse transitions. If two transitions are detected less than 32 ms apart, however, the two transitions are considered valid where the transitions are at least 20 ms apart, if the two transitions are of opposite polarities. In addition, a valid combined pulse transition must be of less than a predetermined duration. In the preferred embodiment, a valid combined pulse transition must be less than 50 ms in duration. The transition duration is simply the difference between the offset and onset of the transition.

The valid transitions identified above are then stored in a linked-list of detected transitions and a transition counter is incremented to indicate the number of valid transitions identified. In the preferred embodiment, the calibration method uses only a predetermined number of valid transitions, e.g., 300, to generate the correction factor. The predetermined number of valid transitions is determined by the expected length of the calibration period and the frequency of the calibration signal.

Referring again to FIG. 1, the valid combined pulse transitions are used to detect combined calibration pulses in step 20. Step 20 requires at least three valid transitions before it can be executed. If there is an insufficient number of valid transitions, step 20 transitions to step 12 (not shown in FIG. 1) and additional waveform data is loaded. Otherwise, the valid transitions are examined to form a combined calibration pulse. A combined calibration pulse is determined where adjacent transitions display a predetermined relationship.

Figure 4A:
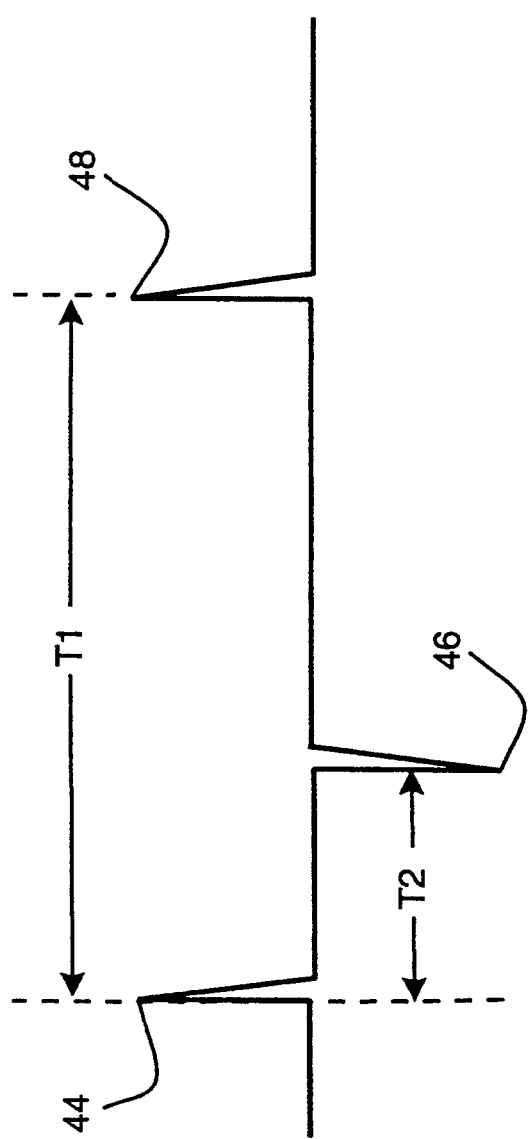
FIG. 4A is a graphical representation of a first sequence of transitions that form a valid combined calibration pulse.
Figure 4B:
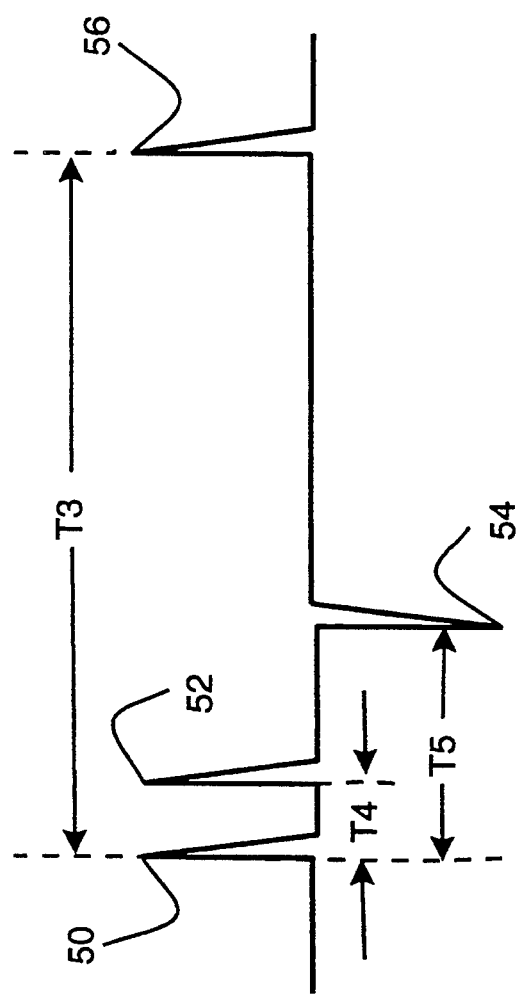
FIG. 4B is a graphical representation of a second sequence of transitions that form a valid combined calibration pulse.

Referring now to FIGS. 4A and 4B, two predetermined relationships are shown. In the first relationship shown in FIG. 4A, a combined calibration pulse is formed where a first transition 44 is positive, a second transition 46 is negative, and a third transition 48 is positive. In addition, transitions 44, 46, and 48 must exhibit a predetermined temporal relationship in order for the series of transitions of FIG. 4A to form a combined calibration pulse. In the preferred embodiment, period T1 must be greater than period T2 and, further, T1 must be less than 600 ms. If transitions 44, 46, and 48 satisfy the above criteria the transitions form a valid combined calibration pulse.

A second sequence of transitions that form a combined calibration pulse is shown in FIG. 4B. In the second relationship, a first positive transition 50 is followed by a second positive transition 52, which is further followed by a negative transition 54 and finally a third positive transition 56. In addition to exhibiting the described relationship, period T4 must be less than 50 ms and period T5 must be greater than 50 ms. If a series of transitions meets these criteria, transition 52 is discarded as an erroneous transition. The sequence shown in FIG. 4B typically results from an overly active transition detection. In the sequence shown in FIG. 4B, transition 50 and transition 54 form a valid combined calibration pulse.

Step 20 further detects the period between successive combined calibration pulses. If the separation or gap between two adjacent combined calibration pulses is greater than 5 minutes, with a total often or fewer combined calibration pulses detected thus far, the earlier detected combined calibration pulses are discarded. These combined calibration pulses are discarded in order to handle significant tape drop-out during calibration pulse recording.

The combined calibration pulses detected in step 20 are used in step 22 to determine onset and offset points for actual calibration pulses on the individual channels. Step 22 correlates the combined calibration pulses to the corresponding channel pulses using a cross-correlation technique to determine the exact onset and offset points for the channel calibration pulses. The cross-correlation method is shown in more detail in FIG. 5.

Correlation Method

Figure 5:
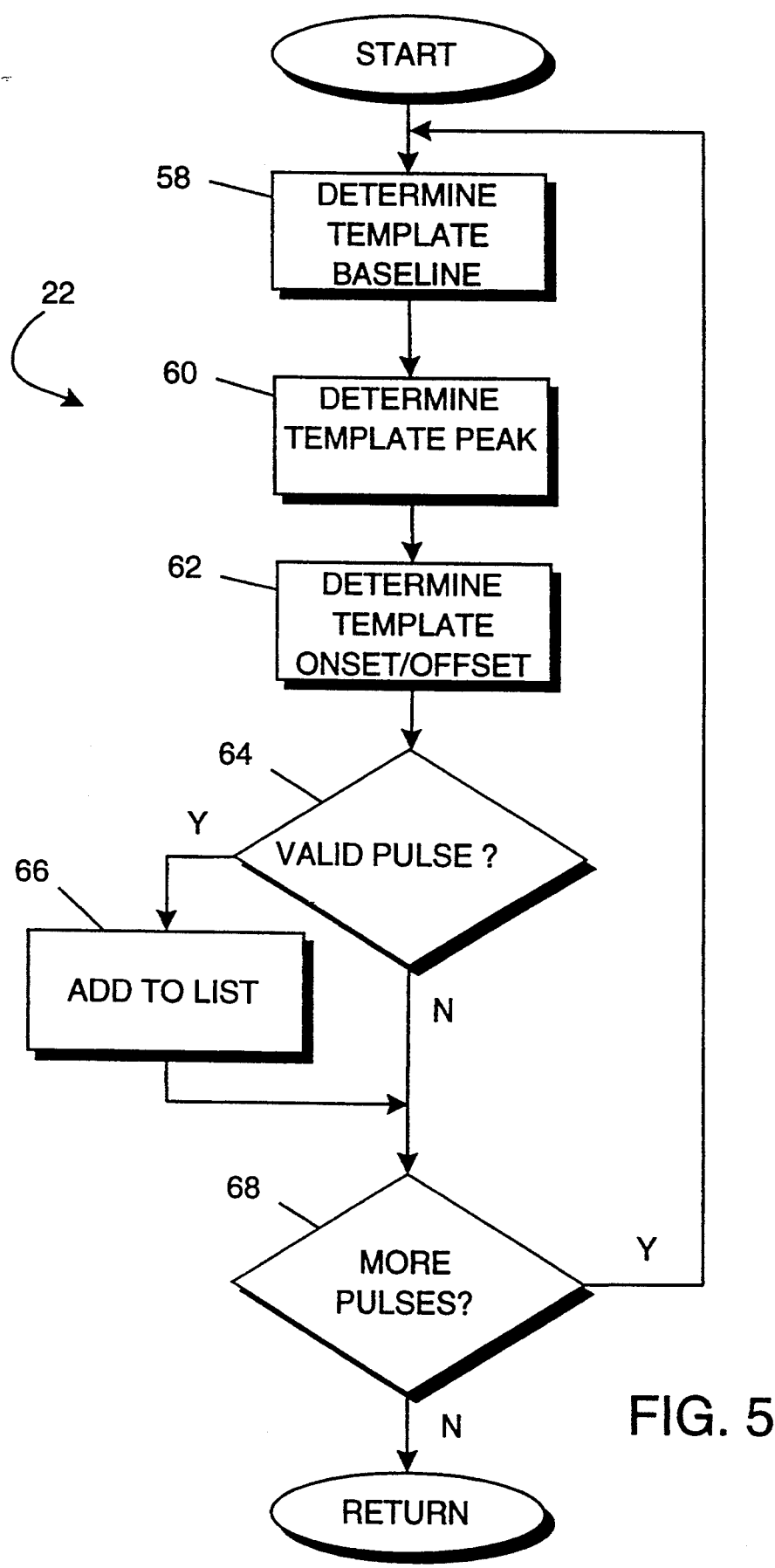
FIG. 5 is a flow chart of the correlation step 22 of FIG. 1 according to the invention.

The correlating steps shown in FIG. 5 are performed for each combined calibration pulse on a corresponding channel pulse in each of the channels. The following description is with respect to a single combined calibration pulse and a corresponding channel calibration pulse. For each combined calibration pulse, however, the steps shown in FIG. 5 are repeated for each channel.

The combined calibration pulse is used in step 22 to set an initial onset and offset of a correlation template. The correlation template is used to define the characteristics of the corresponding channel calibration pulse, i.e. an onset, an offset, a baseline and a peak if a valid channel calibration pulse exists. The resulting correlation template is used to construct an ideal channel calibration pulse as described below.

Referring again to FIG. 5, a template baseline is determined in step 58 by calculating the mean value of the channel waveform data prior to the onset time of the combined calibration pulse. In the preferred embodiment, the mean is calculated between the onset time minus 150 ms and the onset time minus 100 ms. A template peak value is then determined in step 60 as the mean value of the channel waveform data between the onset of the combined calibration pulse and the offset of the combined calibration. In step 62, the template onset and offset times are adjusted until the correlation between the template and the corresponding channel calibration pulse is a maximum as described below. A detailed description of the template onset and offset determination of step 62 is made with reference to FIGS. 6A and 6B, as described herein below. Step 62 adjusts the onset and offsets of the correlation template until the maximum correlation between the template and the corresponding channel calibration pulse is found. If, however, the correlation between the template and the corresponding channel calibration pulse is not greater than a predetermined correlation, the channel calibration pulse is marked as invalid, as described further below with reference to FIGS. 6A and 6B.

Step 64 determines whether the channel calibration pulse was a valid calibration pulse as determined by step 62. If the channel calibration pulse is valid, the channel calibration pulse is added to a list of valid channel calibration pulses in step 66. The valid channel calibration pulses in the list are used to determine a correction scale factor which is used to calibrate the corresponding channel ECG waveform data, as described further below.

Step 68 determines whether or not there are remaining combined calibration pulses. If there are remaining combined calibration pulses, step 68 transitions back to step 58 and a next combined calibration pulse is correlated to a corresponding channel calibration pulse. If there are no more combined calibration pulses, the correlation step 22 is completed and the method transitions to step 24 in FIG. 1. Recall, however, that the correlation step 22 is repeated for each channel.

Figure 6A:
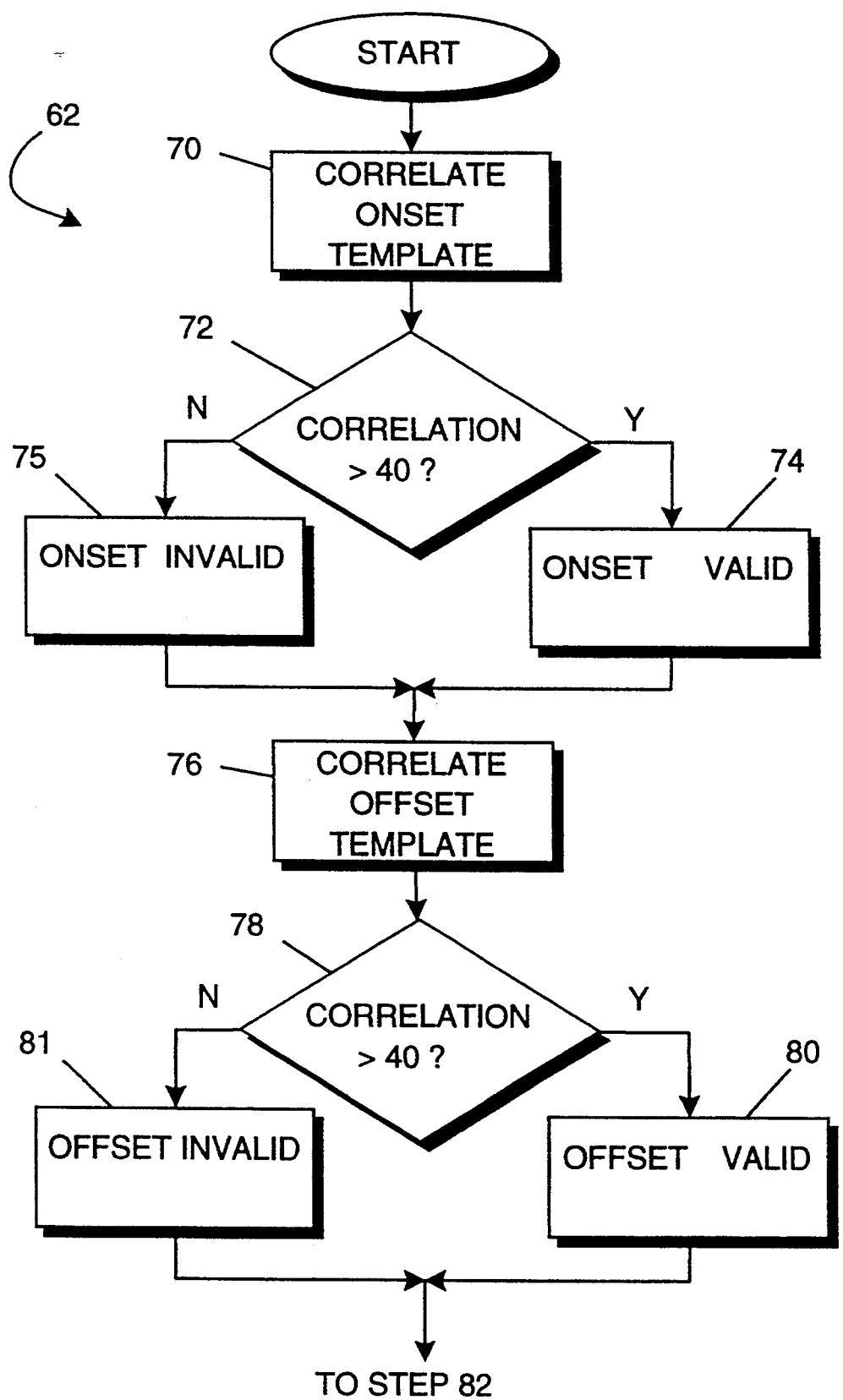
FIGS. 6A and 6B are a flowchart of the template onset and offset determination step 62 of FIG. 5 according to the invention.
Figure 6B:
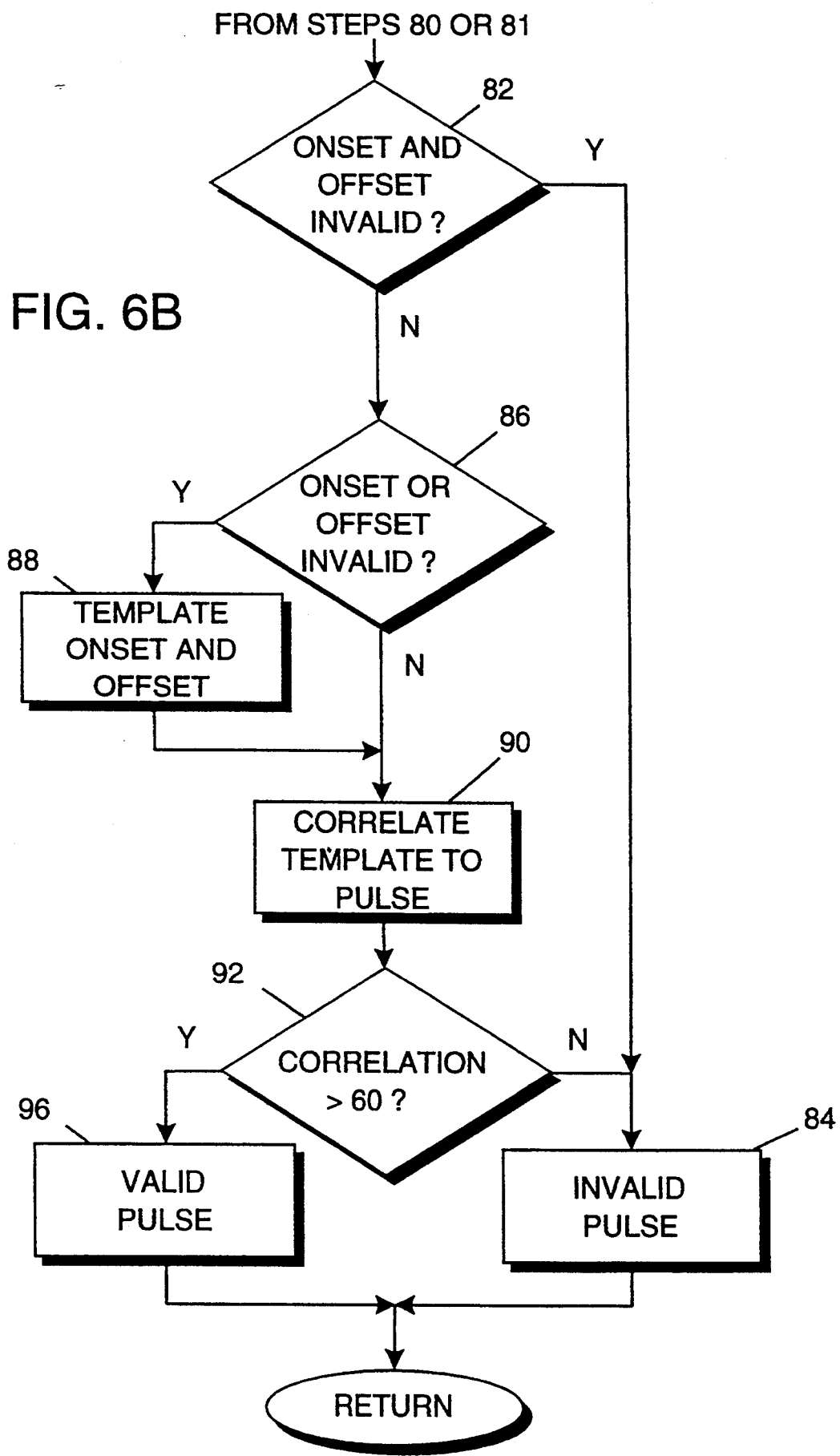

Referring now to FIGS. 6A and 6B, the template onset and offset determination step is shown in more detail. The template onset and offset determination actually comprises three separate correlations to determine the most accurate onset and offset locations of the corresponding channel calibration pulse. In order to perform the three separate correlations, the template is broken up into an onset template and an offset template. The onset template is then correlated to an onset portion of the corresponding channel calibration pulse and the offset template is correlated to an offset portion of the corresponding channel calibration pulse. The onset and offset templates can therefore be adjusted independently to precisely identify the onset and offset locations of the corresponding channel calibration pulse.

The onset template consists of a portion of the correlation template around the onset of the correlation template. In the preferred embodiment, the onset template includes the portion of the correlation template within plus or minus 20 ms of the template onset. Initially, the correlation tern plate onset is set to the onset of the combined calibration pulse. In step 70, the onset template is correlated to the corresponding channel calibration pulse using an area of difference cross correlation technique. The area of difference technique returns a measure of fit between the onset template and the portion channel calibration pulse. For no fit a zero is returned, and for a perfect fit one hundred is returned. Correlation step 70 is successively executed until the correlation between the onset template and the onset portion of the channel calibration pulse is a maximum. Each iteration of correlation step 70 includes the step of adjusting the onset template to a different onset portion of the channel calibration pulse. The onset template is repeatedly adjusted until the maximum correlation between the onset template and the channel calibration pulse is determined.

In step 72, the maximum correlation value determined in step 70 is tested. If the maximum correlation between the onset template and the channel calibration pulse is greater than 40, the onset is marked as valid in step 74. Otherwise, the onset is marked as invalid in step 75.

The offset template is the mirror image of the onset template. The offset template includes the template offset and the template data within plus or minus 20 ms thereabout. In step 76, the offset template is correlated to an offset portion of the channel calibration pulse using the area of difference cross correlation technique as described above. As with the onset template correlation, the offset template correlation is successively repeated until a maximum offset template correlation is identified.

The resulting maximum offset template correlation value determined in step 76 is then tested in step 78. If the maximum offset template correlation value is greater than 40, the offset correlation is set to valid in step 80. If, however, the offset correlation returns a value less than 40, the offset is marked invalid in step 81. The correlation value of 40 was chosen based on empirical data, but the correlation value can be changed without departing from the scope of the invention.

Referring now to FIG. 6B, step 82 determines whether both the onset and offset correlations are invalid. If the onset and offset correlations are both invalid, the channel calibration pulse is identified as invalid in step 84 and the correlation step terminated. If, however, they are both not invalid, step 86 determines whether either the onset or the offset correlations are invalid. If one or the other correlations are invalid, but not both, the template onset and offset values are set back equal to their initial onset and offset values corresponding to the onset and offset points of the combined calibration pulse. Otherwise, the template onset and offset points remain equal to the points at which the maximum correlation occurred.

The resulting correlation template is then correlated to the corresponding channel calibration pulse in step 90. The same area of difference cross correlation technique is used in step 90 as well. The correlation value produced in step 90 is compared to a predetermined correlation value in step 92 to determine whether a valid channel calibration pulse exists. In the preferred embodiment, the predetermined correlation level is equal to 60. Thus, if the correlation value determined in step 90 is greater than 60, the, channel calibration pulse is identified as a valid calibration pulse. However, if the correlation value is less than 60, the channel calibration pulse is identified as an invalid pulse in step 84. The onset and offset correlation step is then complete.

Referring back to FIG. 1, after the combined calibration pulses are correlated to the individual channel pulses in step 22 to determine valid calibration pulses, step 24 determines whether additional ECG data needs to be loaded. If so, step 24 transitions to step 12 to load an additional predetermined amount of ECG waveform data. If, however, all of the ECG data has been loaded and processed by steps 12 through 22, steps 26 through 32 are then executed for each channel using the valid channel calibration pulses determined in step 22.

Step 26 examines the valid calibration pulses in a particular channel to determine a characterization of the valid channel calibration pulses. The purpose behind step 26 is to intelligently account for the various recording conditions in which the calibration pulses were recorded. For example, some ECG recorders may produce calibration pulses of monotonically increasing amplitude as a recorder physically "warms up". In this case, earlier recorded calibration signals would result in an over-compensation of the ECG waveform data. Step 26 characterizes the valid channel calibration pulses according to the distribution of amplitudes among all of the valid channel calibration pulses within the channel. The resulting distribution of calibration pulse amplitudes are classified as either normal, semi-normal, or double-exponential. The characterization is then use to select those valid calibration pulses which most accurately represent the channel recording characteristics.

Step 28 selects the appropriate valid calibration pulses based on the characterization of the valid calibration pulses. If the distribution is normal or semi-normal, all of the valid calibration pulses for the channel are selected. If, however, the distribution is characterized as double exponential, then only the last 100 detected valid calibration pulses are selected.

An average calibration pulse is generated in step 30 using the selected calibration pulses. There must be at least 6 selected calibration pulses in order to generate an average calibration pulse. If the number of selected calibration pulses is less than or equal to 20, a fixed alpha-trimmed mean is used to generate the average calibration pulse. If there are more than 20 selected calibration pulses an adaptive alpha-trimmed mean is used to generate the average calibration pulse. The average calibration pulse is formed by aligning the onsets of the selected calibration pulses and calculating the mean value for each sample using either the fixed or adaptive alpha-trimmed mean.

The average calibration pulse generated in step 30 is used in step 32 to determine a correction scale factor for the corresponding channel. The correction scale factor is derived from the average calibration pulse from a baseline and peek of the average calibration pulse. The baseline of the average calibration pulse is calculated as the mean value from two combined segments taken on either side of the calibration pulse. In the preferred embodiment, the two segments are 50 ms in duration. The peak value of the average calibration pulse is calculated from a segment of the average calibration pulse between an onset and an offset of the average calibration pulse. If the average calibration pulse has a pulse width less than or equal to 50 ms, as measured between the onset and offset, the peak value is equal to the mean value between the onset and offset of the average calibration pulse. If, however, the average calibration pulse width is greater than 50 ms, the peak value is equal to the mean value between the onset plus 20 ms and the offset minus 20 ms.

The difference between the peak and the baseline of the average calibration pulse is used to determine the correction scale factor. The method assumes, a priori, that the calibration pulses were recorded with an amplitude of 1 mV, which is the industry standard. Therefore, the difference between the peak and the baseline of the average calibration pulse is normalized to 1 mV. The factor required to normalize the difference represents the correction scale factor. The correction scale factor is then used to calibrate all of the ECG waveform data loaded off of the corresponding channel. The ECG waveform data is calibrated by dividing the amplitude of the ECG waveform data by the correction scale factor.

In addition to determining the correction scale factor, the calibration method also determines the onset and offset of the calibration pulses in step 34. Step 34 examines all of the valid combined calibration pulses from the beginning until a predetermined number of consecutive calibration pulses is identified with a frequency approximately 1 Hz. If the predetermined number of consecutive calibration pulses is detected, a starting point of the predetermined number of calibration pulses is identified as the onset of the calibration pulses. Similarly, the valid calibration pulses are examined beginning with the last one of the valid calibration pulses until a predetermined number of consecutive calibration pulses are identified. If a predetermined number of calibration pulses are identified, an ending point of a last-occurring calibration pulse in the predetermined number of valid calibration pulses is set to the offset of the calibration pulses. The onset and offset are then used to identify the beginning of the actual EGG waveform data.

Finally, in step 36, the skew between channels is determined. The interchannel skew is determined by comparing the onset times of corresponding valid calibration pulses in the channels. In the preferred embodiment, the mean difference between the onsets of the corresponding calibration pulses is used as the skew. The inter channel skew can therefore be corrected by phase-shifting the patient ECG waveform data by the skew amount.

Having described and illustrated the principles of the invention in a preferred embodiment thereof, it should be apparent that the invention can be modified in arrangement and detail without departing from such principles. We claim all modifications and variation coming within the spirit and scope of the following claims.

We claim:

1. A method of calibrating an ECG ambulatory monitor from calibration pulses recorded on a plurality of tape channels having ECG waveform data, the method comprising:
   loading the channel calibration pulses;
   combining the channel calibration pulses to form a series of combined calibration pulses;
   selecting combined calibration pulses having certain predetermined characteristics;
   correlating the selected combined pulses to the corresponding channel calibration pulses;
   selecting channel calibration pulses having at least a predetermined correlation to the corresponding selected combined pulses;
   generating a calibration scale factor for each channel based on the selected channel calibration pulses for the corresponding channel; and
   calibrating each channel of the ECG monitor using the calibration scale factor.

2. A method of calibrating an ECG ambulatory monitor according to claim 1 wherein selecting combined calibration pulses having certain predetermined characteristics comprises:
   detecting transitions of the combined calibration pulses; and
   selecting a combined calibration pulse where a first detected transition and a second detected transition exhibit a predetermined relationship.

3. A method of calibrating an ECG ambulatory monitor according to claim 2 wherein selecting a combined calibration pulse where a first detected transition and a second detected transition exhibit a predetermined relationship includes:
   detecting, in order, a first transition, a second transition, and a third transition;
   measuring a time period between the first transition and the third transition; and
   selecting a combined calibration pulse where the time period is less than a predetermined maximum period, wherein the first transition defines an onset of the selected combined pulse and the second transition defines an offset of the combined calibration pulse.

4. A method of calibrating an ECG ambulatory monitor according to claim 2 wherein selecting a combined calibration pulse where a first detected transition, and a second detected transition exhibit a predetermined relationship includes:
   detecting, in order, a first transition, a second transition, a third transition, and a fourth transition;
   measuring a time period between the first transition and the second transition; and
   selecting a combined calibration pulse where the time period is less than a predetermined maximum period, wherein the first transition defines an onset of the selected combined pulse and the third transition defines an offset of the combined calibration pulse.

5. A method of calibrating an ECG ambulatory monitor according to claim 2 further comprising removing, prior to the selecting step, transitions whose amplitudes are less than a predetermined threshold.

6. A method of calibrating an ECG ambulatory monitor according to claim 5 wherein the step of removing transitions whose amplitude are less than a predetermined threshold includes removing transitions whose amplitudes are less than $\frac{1}{4}$ of a maximum peak amplitude of the transitions.

7. A method of calibrating an ECG ambulatory monitor according to claim 1 wherein the step of correlating the combined calibration pulses to the corresponding channel calibration pulses includes:
   forming a calibration pulse template for each channel calibration pulse from a corresponding combined calibration pulse, the calibration pulse template having an onset, an offset, a baseline, and a peak;
   correlating the calibration pulse template to the corresponding channel calibration pulse;
   adjusting the onset and the offset of the template to maximize the correlation between the template and the corresponding channel calibration pulse;
   forming an ideal calibration pulse having the adjusted onset, the adjusted offset, the baseline, and the peak of the calibration pulse template;
   correlating the ideal calibration pulse to the corresponding channel calibration pulse; and
   selecting the channel calibration pulse where the correlation between the ideal calibration pulse and the corresponding channel calibration pulse exceeds a predetermined correlation value.

8. A method of calibrating an ECG ambulatory monitor according to claim 7 wherein the step of forming a calibration pulse template includes forming: an onset template and an offset template and the template correlating step includes:

correlating the on set template to an onset portion of the corresponding channel calibration pulse proximately located to the combined calibration pulse onset;

adjusting the onset template to maximize the correlation between the onset template and the onset portion of the channel calibration pulse;

identifying the onset of the ideal calibration pulse as a point wherein the template correlation is at a maximum if the template correlation is greater than a predetermined onset correlation value; and identifying the onset of the ideal calibration pulse as the onset of the corresponding combined calibration pulse if the correlation is less than or equal to the predetermined onset correlation value.

9. A method of calibrating an ECG ambulatory monitor according to claim 7 wherein the step of forming a calibration pulse template includes forming; an onset template and an offset template and the template correlating step includes:

correlating the offset template to an offset portion of the channel calibration pulse proximately located to the combined calibration pulse offset;

adjusting the offset template to maximize the correlation between the offset template and the offset portion of the channel calibration pulse;

identifying the offset of the ideal calibration pulse as a point wherein the template correlation is at a maximum if the template correlation is greater than a predetermined offset correlation value; and identifying the offset of the ideal calibration pulse as the offset of the corresponding combined calibration pulse if the template correlation is less than or equal to the predetermined offset correlation value.

10. A method of calibrating an ECG ambulatory monitor according to claim 7 wherein the step of forming a calibration pulse template includes determining a mean baseline value from a number of samples of the corresponding channel calibration pulse taken prior to the template onset.

11. A method of calibrating an ECG ambulatory monitor according to claim 7 wherein the step of forming a calibration pulse template includes determining a mean peak value from samples of the corresponding channel calibration pulse taken between the template onset and offset.

12. A method of calibrating an ECG ambulatory monitor according to claim 1 wherein the step of combining the calibration pulses to form combined calibration pulses includes combining the calibration pulses using a sum of absolute value method (SABSV).

13. A method of calibrating an ECG ambulatory monitor according to claim 1 further comprising:

characterizing the selected calibration pulses as having a normal, seminormal, or double-exponential distribution;

calibrating each channel of the ECG monitor according to the corresponding selected calibration pulses if the distribution is normal or seminormal; and calibrating each channel of the ECG monitor according to a predetermined number of last selected calibration pulses if the distribution is double-exponential.

14. A method of calibrating an ECG ambulatory monitor according to claim 1 wherein the step of generating a calibration scale factor for each channel based on the selected channel calibration pulses for the corresponding channel includes:

generating an average calibration pulse for each channel from the selected calibration pulses of the corresponding channel;

defining an onset and an offset on the average calibration pulse;

determining a mean baseline value of the average calibration pulse;

determining a mean peak value of the average calibration pulse;; and determining a correct ion scale factor equal to the difference between the mean peak value and the mean baseline value.

15. A method of calibrating an ECG ambulatory monitor according to claim 14 wherein the step of generating an average calibration pulse includes:

generating an average calibration pulse using a fixed alpha-trimmed mean method if the number of selected calibration pulses is less than or equal to a predetermined number of pulses; and generating an average calibration pulse using an adaptive alpha-trimmed mean method if the number of selected calibration pulses is greater than the predetermined number of pulses.

16. A method of calibrating an ECG ambulatory monitor according to claim 1 further comprising:

detecting for each channel a second predetermined number of consecutive selected pulses having a last selected calibration pulse as a last detected pulse in the second predetermined number; and setting an end of the calibration data equal to an offset of the last detected pulse.

* * * * *